(12) United States Patent
Cook

(10) Patent No.: US 6,487,728 B1
(45) Date of Patent: Dec. 3, 2002

(54) MALE SHEATH UNDERWEAR/BANDAGE

(76) Inventor: Ronald Nelson Cook, P.O. Box 2245, Red Bank, NJ (US) 07701

( * ) Notice: Subject to any disclaimer, the term of this patent is extended or adjusted under 35 U.S.C. 154(b) by 0 days.

(21) Appl. No.: 09/954,539

(22) Filed: Sep. 17, 2001

(51) Int. Cl.[7] .................................................. A41B 9/02
(52) U.S. Cl. ............................................. 2/403; 602/67
(58) Field of Search ...................... 2/400, 403; 602/60, 602/61, 67, 68, 70, 73

(56) References Cited

U.S. PATENT DOCUMENTS

| | | | | |
|---|---|---|---|---|
| 796,278 A | * | 8/1905 | Zangmeister | 602/67 |
| 850,298 A | * | 4/1907 | De Mars | 602/67 |
| 1,477,187 A | * | 12/1923 | Rayne | 602/67 |
| 1,686,943 A | * | 10/1928 | Tritch | 602/6 |
| 2,888,014 A | * | 5/1959 | Dougherty | 602/67 7 |
| 3,550,590 A | * | 12/1970 | Keilman | 602/67 |
| 4,590,931 A | * | 5/1986 | Kidwell, Jr. | 602/67 |
| 4,981,147 A | * | 1/1991 | Barnett | 602/67 |
| 5,237,706 A | * | 8/1993 | Nalbandian | 2/403 |

OTHER PUBLICATIONS

Undergear Catalog, Fall 1993, pp. 2–3, Items F–G, Cotton/Spandex Underwear.*

* cited by examiner

Primary Examiner—Gloria M. Hale

(57) ABSTRACT

This male penis sheath underwear/bandage is worn in place of the traditional male underwear brief or boxer short. The form of the tubular sheath follows that of the penis. The tubular sheath is open at each end and is provided with a slit at the proximal end through which the scrotum is passed. The garment is unique in that it is self-securing, requiring no waistbands or leg straps. Also, the sheath does not have to be removed in order to urinate.

2 Claims, 1 Drawing Sheet

MALE SHEATH UNDERWEAR/BANDAGE

CROSS-REFERENCE TO RELATED APPLICATIONS (Not Applicable)

FEDERALLY SPONSORED RESEARCH OR DEVELOPMENT (Not Applicable)

A MICROFICHE APPENDIX (Not Applicable)

BACKGROUND

1. Field of Invention

This invention relates to male wearing apparel, specifically to apparel worn under trousers as underwear.

The traditional male undergarment is the brief, boxer short, bikini, thong, or athletic supporter or cup. Also included in this list are various medical or surgical bandages. Each of these garments shares a common characteristic of a single-pouch construction for holding the two principle parts of the male genitalia: the penis and the scrotum. This construction compacts the male genitalia, causing abrasion (chafing), sticking, misalignment, itching, and fosters perspiration that could lead to a fungal infection.

It is the intent of this invention to eliminate most of the discomforts (as described above) exhibited by conventional male underwear.

2. Related Art

Many types of male undergarments that offer protection for the penis exist in prior art. U.S. Pat. No. 2,888,014 describes a suspensory with a pouch that supports the penis and scrotum. U.S. Pat. No. 1,686,943, depicts an athletic supporter that protects the penis and scrotum, while providing a means for recording a striking blow to this area of the body. U.S. Pat. No. 850,298 delineates a suspensory that provides protective pouches for both the penis and the scrotum. U.S. Pat. No. 5,237,706 describes a male garment with a scrotal pouch that repositions both the penis and the scrotum to a more prominent anterior position. U.S. Pat. No. 796,278 depicts a supporter for the scrotum to be used during the treatment of a number of male diseases. U.S. Pat. No. 3,550,590 describes a pouch-like surgical bandage to protect the penis and/or scrotum after injury or surgery.

U.S. Pat. No. 1,477,187 depicts a surgical appliance that supports a suspensory, a pouch, or both to protect the penis and scrotum. Although these seven prior art describe male undergarments that protect the penis and scrotum, each of them relies on waistbands and/or leg straps to secure the protective device to the male body. Whereas, my invention, which protects the penis, is without the encumbrances of a waistband or leg straps.

U.S. Pat. No. 4,590,931 describes a protecting scrotum guard, which uses hook and loop fastening strips as the retention device to protect the penis, the scrotum, or both. My invention offers two advantages over this guard: (1) it is less bulky, mine being a single tubular sheath, and (2) it does not have to be removed in order to urinate.

The Undergear catalog, fall 1993, page 2, Items F-J, Tactics Contour (Registered) Collection, details traditional elasticized cotton garments of various leg lengths, i.e., above the knee, below the knee, to the upper thigh, and to the ankle. My invention is made of similar material (elasticized cotton), but covers only the penis.

U.S. Pat. No. 4,981,147 details a disposable, unitary coital protective garment, comprising a groin-covering panel and an integrally formed penile sheath. This art is not meant for every-day use and does not allow for urination without its removal. My invention is designed for every-day use and does not have to be removed in order to urinate.

SUMMARY OF INVENTION

The design of this invention provides a one-piece garment with clean, simple lines that does not distort, deform, or interfere with the natural shape and functioning of the male genitals. The garment also accommodates the natural changes in size and shape that occur with the penis and scrotum.

The simplicity of the garment allows comfort to the wearer no matter what the activity, eliminating most of the discomforts inherent in conventional undergarments: constriction, friction, chafing, and distortion. The penis is protected and the scrotum remains free from cramping and squeezing.

The garment is also adaptable as a surgical or medical bandage.

Shown in FIG. 1 are

Figure 1:
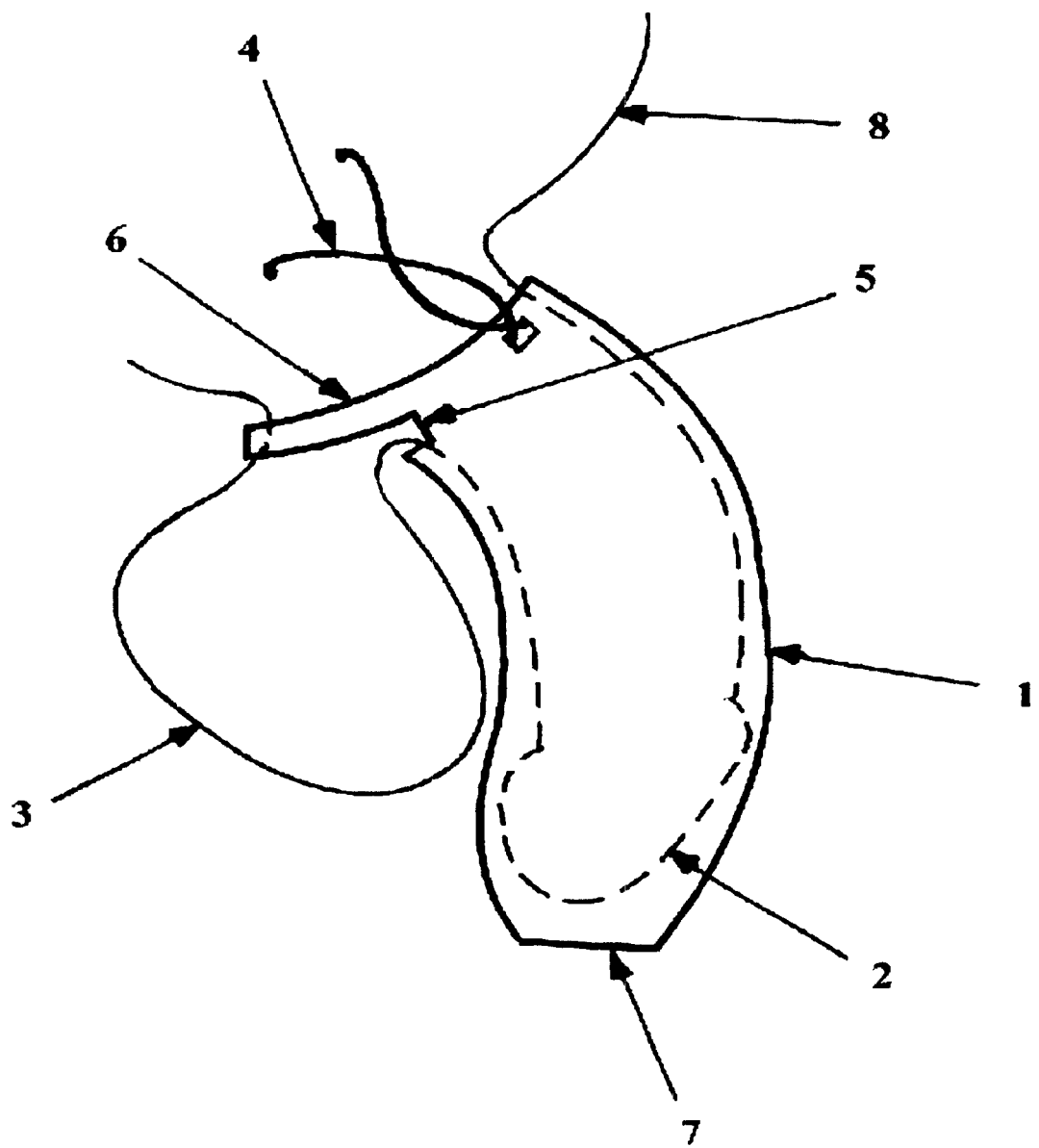
FIG. 1 is a side view of this invention. It shows the Male Sheath as it is worn. It shows the sheath covering the penis for its entire length. The scrotum is shown after having been passed through the slit provided at the proximal end of the sheath.

1. Male Sheath
2. Penis
3. Scrotum
4. Drawstring (optional, see claim 2)
5. Slit
6. Proximal end (retaining closure)
7. Distal end
8. Abdomen.

DETAILED DESCRIPTION

The male underwear of this invention is made from elasticized cotton in the shape of a tube, open at each end. This tubular sheath (1) conforms to the shape of the penis (2). A slit (5) is provided on the underside of the garment through which the scrotum (3) is passed. The length of the slit is approximately one-third the circumference of the tubular sheath.

When worn, the penis and scrotum are inserted into the tube and the scrotum is then passed through the slit. The sheath now covers the penis and the sheath remains in place and secure.

This invention protects the penis from friction that might occur when worn under trousers, especially trousers made of a rough fabric like denim. The scrotum is also protected from being cramped and squeezed.

This invention would be manufactured in a number of sizes that would accommodate the variety of lengths and diameters of the penis.

ADVANTAGES

This invention provides the male wearer with the following advantages:

1. An improved garment to be worn as underwear.
2. An underwear garment that follows the natural separation between the penis and the scrotum.
3. An underwear garment that accommodates and protects the ever-changing shape and movement of the male genitals.
4. An underwear garment that provides a sense of freedom.
5. An underwear garment that is free of binding waistbands and/or leg straps.
6. An underwear garment that requires no awkward fly construction, yet provides easy access for urination.
7. An underwear garment that provides protection for the circumcised penis.
8. An underwear garment that can also be use as a medical or surgical bandage.

What is claimed is:

1. A male garment for the protection of the penis comprised of a one-piece elasticized cotton tubular sheath sized to cover a penis; said tubular sheath includes two open ends including a proximal end opening closest to the wearer's body having a retaining closure to retain the sheath around the base of the wearer's penis and scrotum; said sheath includes a distal end opening that allows for urination by the wearer without the removal of the sheath; said tubular sheath includes a slit adjacent the proximal end opening retaining closure; said slit has a length that is approximately one-third of the length of the circumference of the sheath; whereby, when the wearer's penis and scrotum are passed through the proximal end opening and the scrotum is then inserted through the slit, is then uncovered and assists in the securement of the sheath to the wearer without the use of a waistband or leg straps.

2. The male garment as claimed in claim 1 wherein the proximal end opening retaining closure includes any one of a drawstring, a snap, hook and loop strips, or any combination thereof.

* * * * *